United States Patent [19]

Dahne

[11] Patent Number: 4,856,647

[45] Date of Patent: Aug. 15, 1989

[54] APPARATUS FOR CONNECTING CONTAINERS

[76] Inventor: Cynthia F. Dahne, 4 Tentmill La., Apartment C, Baltimore, Md. 21208

[21] Appl. No.: 234,155

[22] Filed: Aug. 19, 1988

[51] Int. Cl.[4] ............................................. A45C 11/04
[52] U.S. Cl. ..................................... 206/5.1; 206/431; 206/223; 206/568; 206/570; 206/581; 220/23.2; 220/23.4; 220/23.83
[58] Field of Search ................ 206/5.1, 150, 217, 427, 206/431, 432, 223, 568, 570, 581; 220/23.2, 23.4, 23.83, 85 H; 229/1.5 H; 224/918, 919

[56] References Cited

U.S. PATENT DOCUMENTS

| | | | |
|---|---|---|---|
| 2,882,087 | 4/1959 | Socke | 206/431 |
| 3,326,358 | 6/1967 | Singleton | 206/5.1 |
| 3,640,018 | 2/1972 | Light | 220/23.83 |
| 3,682,352 | 8/1972 | Doucette | 206/150 |
| 3,695,280 | 10/1972 | Sturgeon | 206/5.1 |
| 3,702,203 | 10/1970 | Oltmanns | 206/150 |
| 3,751,082 | 8/1973 | Somerville | 220/23.83 |
| 3,785,484 | 1/1974 | Cunningham . | |
| 3,823,814 | 7/1974 | Lum . | |
| 3,856,571 | 12/1974 | Sherman | 206/5.1 |
| 3,891,174 | 6/1975 | Harvey . | |
| 3,930,578 | 1/1976 | Stein . | |
| 4,061,256 | 12/1977 | Beer et al. | 224/919 |
| 4,062,510 | 12/1977 | Brochu . | |
| 4,089,412 | 5/1978 | Baugh . | |
| 4,103,811 | 8/1978 | Owen | 206/150 |
| 4,377,234 | 3/1983 | Kaplan | 206/432 |
| 4,390,095 | 6/1983 | Cunningham . | |
| 4,537,341 | 8/1985 | Kelly . | |
| 4,544,194 | 10/1985 | Allen | 206/150 |
| 4,620,631 | 11/1986 | Bartelt | 220/85 H |
| 4,686,745 | 8/1987 | Butler . | |

Primary Examiner—David T. Fidei
Attorney, Agent, or Firm—Roylance, Abrams, Berdo & Goodman

[57] ABSTRACT

An apparatus for connecting containers to each other. The apparatus has three of elastic loops which compressively secure three containers inserted therein. One loop is oriented with respect to two other loops such that its longitudinal axis is substantially perpendicular to the longitudinal axes of the two other loops and is saubstantially perpendicular to the plane defined by the longitudinal axes of the two other loops. The apparatus has particular advantages in connecting together cleaning solution containers for contact lenses and a case for storing contact lenses.

11 Claims, 2 Drawing Sheets

APPARATUS FOR CONNECTING CONTAINERS

FIELD OF THE INVENTION

The invention relates to an apparatus for connecting containers to each other. More specifically, the invention relates to an apparatus having a three elastic loops which compressively secure three containers inserted therein, two containers being oriented in a first attitude and the third container being oriented in a second attitude perpendicular to the first.

BACKGROUND OF THE INVENTION

In a wide variety of environments, ingredients from the same group of containers are repetitively used together in certain procedures. For this reason, conveniency and efficiency in accessing these ingredients can be improved by connecting together the containers in the group such that the containers can be easily retrieved and transported together as a single unit. For example, in a pharmaceutical environment, pills or fluids, each stored in a separate container, are frequently combined with pills or fluids from other containers. If containers in the group can be connected together such that they can be readily accessed as a single unit, the user can avoid the time consuming task of gathering together the individual containers.

Containers which store various cleaning solutions for contact lenses as well as the container for storing the lenses are particularly well suited for grouping together. A soft contact lenses user typically follows a cleaning procedure of cleaning the lenses with a daily lens cleaning solution from one bottle, pouring a saline solution from another bottle into a specially designed contact lens case which stores each lens separately in a saline bath compartment, and then placing the lenses in the case. Accordingly, such users must repetitively gather together the daily cleaner bottle, the saline solution bottle and contact lens case to perform the cleaning procedure. An apparatus which connects together these containers would improve the convenience and efficiency of the cleaning operation by allowing the user to grasp and move the containers as a single unit and to keep the containers together as a single unit.

Several packages or similar devices have been proposed for holding containers or other elements together as a group. For example, see U.S. Pat. Nos. 3,785,484 to Cuniingham; 3,823,814 to Lum; 3,891,174 to Harvey; 3,930,578 to Stein; 4,062,510 to Brochu; 4,089,412 to Baugh; 4,390,095 to Cunningham; 4,537,341 to Kelly; and 4,686,745 to Butler. However, the need still exists for an apparatus which connects together containers in such a way that the containers are properly and easily oriented with respect to one another and to the surface upon which they are placed and are easily transported as a group.

SUMMARY OF THE INVENTION

Accordingly, it is a primary object of the present invention to provide an apparatus for connecting containers together in an economical fashion.

Another object of the invention is to provide an apparatus for connecting containers together which can accommodate containers of various widths and diameters.

Another object in the invention is to provide an apparatus for connecting containers together which adjusts itself to the varying width or diameter of each of the connected containers.

Yet another object in the invention is to provide an apparatus for connecting containers together which holds containers in a predetermined orientation relative to one another when one or several of the containers are rested on a surface.

A further object of the invention is to provide an apparatus for connecting containers together which spaces the containers from each other by a predetermined amount.

An additional object of the invention is to provide an apparatus for connecting containers together which is specially adapted to connect together cleaning solution containers and storage containers used with contact lenses for easy use, storage and transport.

The foregoing objects are basically attained by providing a connecting assembly for connecting together first, second and third elements, the combination comprising a first elastic loop for receiving the first element, the first elastic loop having a longitudinal axis A; a second elastic loop for receiving the second element, the second elastic loop having a longitudinal axis B substantially parallel to the axis A, the axes A and B defining a plane; means, coupled to the first and second elastic loops, for coupling the first and second elastic loops together; a third elastic loop for receiving the third element having a longitudinal axis C substantially perpendicular to the axes A and B and substantially perpendicular to the plane; and means, coupled to the first and third elastic loops, for coupling the first and third elastic loops together.

Other objects, advantages, and salient features of the present invention will become apparent from the following detailed description, which, taken in conjunction with the annexed drawings, discloses preferred embodiments of the invention.

BRIEF DESCRIPTION OF THE DRAWINGS

Referring now to the drawings which form a part of this original disclosure.

DETAILED DESCRIPTION OF THE INVENTION

Figure 1:
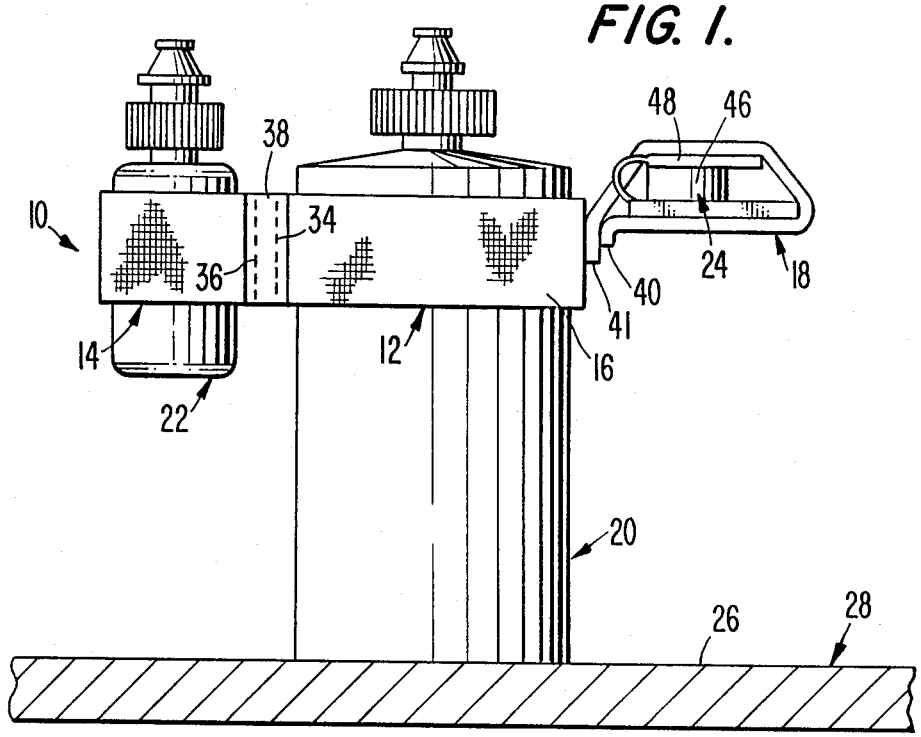
FIG. 1 is a side elevational view of the apparatus of the present invention having a pair of elastic loops compressively gripping first and second containers and another loop compressively gripping a contact lens case.
Figure 2:
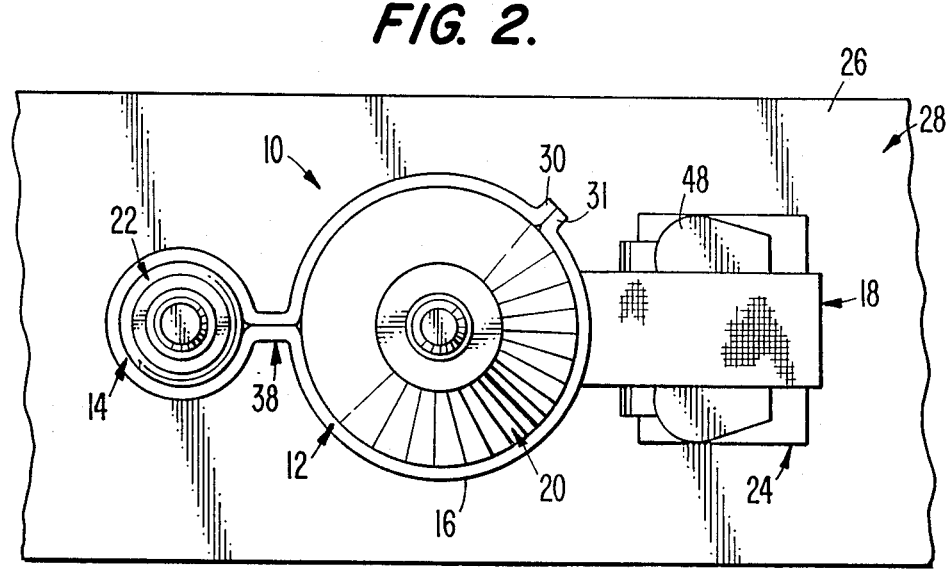
FIG. 2 is a top plan view of the apparatus and interconnected containers shown in FIG. 1 with the pair of elastic loops encircling the diametral periphery of the first and second containers and the third loop encircling the contact lens case.
Figure 3:
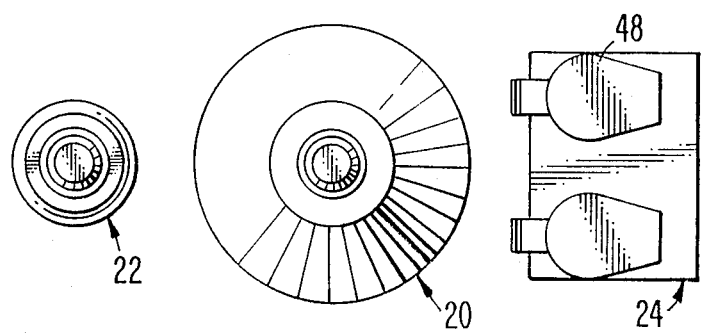
FIG. 3 is a top plan view of the first and second containers and contact lens case of FIG. 1 showing their relative orientation to, and spacing from, one another when interconnected by the apparatus, which is not shown in this figure.

As seen in FIGS. 1–3, apparatus 10 of the present invention includes a first flexible, elastic loop 12 and a second flexible, elastic loop 14 both formed from the same elastic band 16 closed upon itself. Apparatus 10 also includes a third flexible, elastic loop 18 formed of a single elastic band closed upon itself and coupled to first elastic loop 12.

First elastic loop 12 compressively grips a first cylindrical container 20 via its inherent elastic bias. Second elastic loop 14 similarly compressively grips a second cylindrical container 22 and third elastic loop 18 similarly compressively grips a contact lens case 24. In the preferred embodiment, first container 20 is a saline solution container and second container 22 is a daily cleaning solution container. These containers are commercially available in sizes such that first container 20 has a longer longitudinal dimension and greater diameter than second container 22.

The bottom of first container 20 is horizontally supported by the horizontal planar surface 26 of a table or counter top 28. Apparatus 10 is positioned at a vertical height of a few inches above surface 26 such that second container 22 and contact lens case 24 are suspended above surface 26. Thus, first container 20 acts as a vertical support for the interconnected second container 22 and contact lens case 24.

Figure 4:
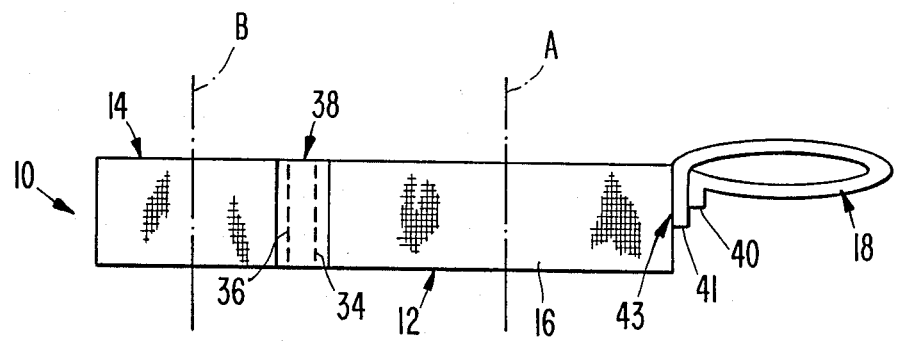
FIG. 4 is a side elevational view of the apparatus of FIG. 1 shown in its relaxed state when no containers are gripped by its loops.
Figure 5:
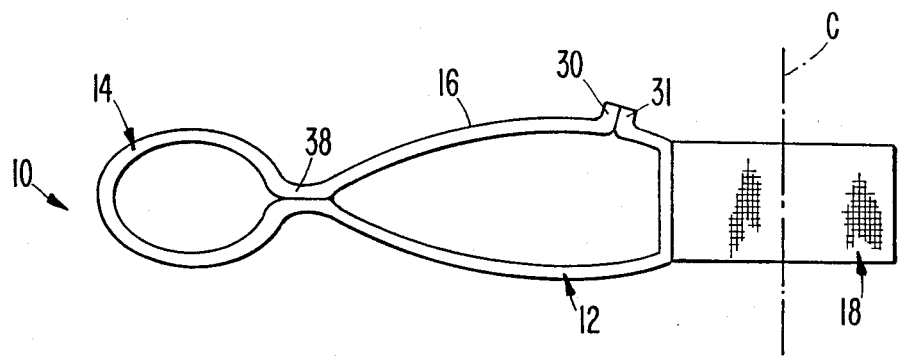
FIG. 5 is a top plan view of the apparatus shown in FIG. 4.
Figure 6:
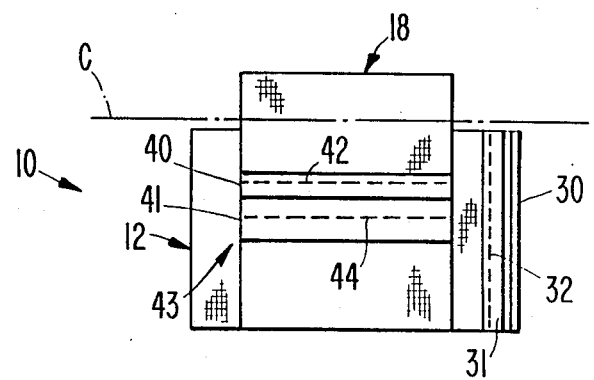
FIG. 6 is an enlarged end elevational view of the, apparatus shown in FIGS. 4 and 5, as viewed from the right-hand side of FIGS. 4 and 5.

Referring now to FIGS. 4–6, first elastic loop 12, second elastic loop 14 and third elastic loop 18 are in a relaxed, unstretched state before any containers are inserted therein. Advantageously, first elastic loop 12 and second elastic loop 14 are substantially oval when relaxed and formed from elastic band 16 by stitching together opposite ends 30 and 31 of elastic band 16 with stitching 32 and by stitching two contacting portions of elastic band 16 together with a pair of parallel stitches 34 and 36. Parallel stitches 34 and 36 are appropriately spaced from one another to form a spacing extension 38 therebetween which spaces first elastic loop 12 from second elastic loop 14. First and second elastic loops 12 and 14 are in a side by side orientation and are substantially coplanar. The peripheral dimensions of the three loops are smaller than the peripheral dimensions of the elements to be received therein.

Elastic band 16 and third elastic loop 18 are advantageously composed of elastic band webbing having a relaxed thickness of about 1/16th inch. Other compositions of material, such as non-elastic material coupled with elastic material, can also be used.

First elastic loop 12 has a central longitudinal axis A and second elastic loop 14 has a central longitudinal axis B. Axes A and B define a plane P (not shown). Axes A and B are substantially perpendicular to surface 26 when apparatus 10 interconnects first container 20, second container 22 and contact lens case 24, and first container 20 rests on surface 26.

Third elastic loop 18 is formed by stitching together its pair of opposite end lengths 40 and 41 with stitching 42 to form a tab 43. Tab 43 is coupled to the first elastic loop 12 by stitching the longer of the pair of opposite end lengths 41 to elastic band 16 with stitching 44. Third elastic loop 18 has a central longitudinal axis C and is substantially oval when relaxed. Third elastic loop 18 is oriented with respect to elastic band 16 that axis C is substantially perpendicular to axes A and B and is substantially perpendicular to plane P. Accordingly, in the preferred embodiment, axis C is substantially perpendicular to axes A and B, and plane P and is substantially parallel to surface 26.

Due to the novel orientation of third elastic loop 18 with respect to first elastic loop 12 and second elastic loop 14, apparatus 10 is ideally suited for interconnecting first container 20, second container 22 and contact lens case 24. Contact lens case 24 is of a type commercially available and includes a pair of cups 46, each for receiving a respective contact lens (not shown) and a pair of sealing caps 48 for sealingly closing cups 46. The user typically pours an amount of the saline solution in first container 20 into each cup 46, places a lens in the saline bath in each of the cups and closes caps 48 to sealingly retain the lenses in cups 46.

To optimally bathe each lens while stored in cups 46 and to minimize leakage of the saline bath from each cup, it is preferable to maintain contact lens case 24 in a horizontal position. Similarly, to minimize leakage from containers 20 and 22, it is preferable to maintain these containers in a vertically upright position. Apparatus 10 is advantageously constructed to maintain containers 20 and 22 and contact lens case 24 in their respective preferred orientations when they are connected together as seen in FIGS. 1 and 2.

The operation of apparatus 10 to interconnect first container 20, second container 22 and contact lens case 24 is as follows. First container 20 is inserted into first elastic loop 12 so as to stretch loop 12 uniformly radially outwardly whereby the loop compressively grips the diametral periphery of first container 20. Likewise, second container 22 is inserted into second elastic loop 14 so that loop 14 compressively grips the container about its diametral periphery. First elastic loop 12 can be positioned along the longitudinal length of first container 20 so that, for example, the bottom of second container 22 is suspended above surface 26 when first container 20 is rested on surface 26, as shown in FIG. 1. Alternatively, first elastic loop 12 can be adjusted along the longitudinal length of first container 20 such that the bottom of second container 22 also rests on surface 26 when the bottom of first container 20 rests on surface 26.

Contact lens case 24 is inserted into third elastic loop 18 such that the case is horizontally oriented and longitudinally centered with respect to axis C of the loop. Third elastic loop 18 thereby compressively grips case 24 about the mid portion of the case. As seen in FIG. 1, case 24 can be positioned within loop 18 such that, when left free-standing, the case projects substantially horizontally, that is, substantially parallel to surface 26. When so oriented, the lenses in cups 46 are optimally bathed in the saline solution therein and, since caps 48 are substantially horizontal relative to the tops of cups 46, leakage of saline solution from the contact lens case 24 is minimized.

First container 20, second container 22 and contact lens case 24 can be inserted into their respective loops in any particular order. Also, the orientation of each loop relative to the longitudinal length of each container or case can be adjusted as desired once the container or case has been inserted into the loop.

Although the preferred embodiment of apparatus 10 comprises stitching to fasten the ends of elastic band 16 and third elastic loop 18 as well as to form spacing portion 38 and couple the first and third loops 12 and 18, the invention also comprehends use of other suitable fasteners such as rivets, adhesive, staples or metal clasps. Also, the invention can be used to interconnect all types of containers or cases and is not limited to use with contact lens containers and cases.

While the invention has been described and illustrated with respect to a preferred embodiment, it will be understood by those skilled in the art that various changes and modifications can be made therein without departing from the scope of the invention as defined in the appended claims. For example, rather than two stitches 34 and 36 being used between loops 12 and 14, only a single line of stitching can be used. In addition, opposite ends 30 and 31 can be overlapped and stitched together, and this overlap can be located between end lengths 40 and 41. Moreover, end lengths 40 and 41 can be made to have the same dimension which can be the vertical thickness of band 16, with stitching 42 and 44 being located near the top and bottom, respectively, of band 16.

What is claimed is:

1. An apparatus for storing contact lenses and cleaning material for cleaning contact lenses, the combination comprising:
    a contact lens case for storing the contact lenses;
    a first container for storing a saline solution for cleaning contact lenses;
    a second container for storing a daily contact lens cleaning material; and
    a connecting assembly for connecting together said contact lens case, said first container and said second container,
    said connecting assembly including
        a first elastic loop for receiving said first container, said first elastic loop having a longitudinal axis A,
        a second elastic loop for receiving said second container, said second elastic loop having a longitudinal axis B substantially parallel to said axis A, said axes A and B defining a plane,
        means, coupled to said first and second elastic loops, for coupling said first and second elastic loops together,
        a third elastic loop for receiving said contact lens case, said third elastic loop having a longitudinal axis C substantially perpendicular to said axes A and B and substantially perpendicular to said plane, and
        means, coupled to said first and third elastic loops, for coupling said first and third elastic loops together.

2. An apparatus as claimed in claim 1, wherein each of said first, second and third elastic loops comprise elastic fabric.

3. An apparatus as claimed in claim 1, wherein said means for coupling said first and second loops together includes stitching.

4. An apparatus as claimed in claim 1, wherein said means for coupling said first and third loops together includes stitching.

5. An apparatus as claimed in claim 1, wherein said means for coupling said first and third elastic loops together includes a tab, coupled to said first elastic loop and to said third elastic loop, for spacing said first elastic loop from said third elastic loop.

6. An apparatus as claimed in claim 1, wherein said means for coupling said first and second elastic loops together includes an extension, coupled to said first elastic loop and to said second elastic loop, for spacing said first elastic loop from said second elastic loop.

7. An apparatus as claimed in claim 1, wherein each of said first and second containers has a longitudinal axis substantially coincident with said axes A and B and said contact lens case has a longitudinal axis substantially coincident with said axis C.

8. An apparatus as claimed in claim 1, wherein said first and second elastic loops are oriented in a side by side relationship.

9. An apparatus as claimed in claim 1, wherein said first, second and third elastic loops are substantially aligned in a side by side relationship.

10. An apparatus as claimed in claim 1, wherein said means for coupling said first and third elastic loops together comprises means for coupling said third elastic loop to said first elastic loop at a single location along said first elastic loop.

11. An apparatus as claimed in claim 1, wherein said first elastic loop has first and second ends, said second elastic loop being located at said first end and said third elastic loop being located at said second end.

* * * * *